United States Patent [19]
Mordon et al.

[11] Patent Number: 5,330,517
[45] Date of Patent: Jul. 19, 1994

[54] DEVICE FOR TREATING TISSUE BY PULSE SEQUENCE GROUP

[75] Inventors: Serge Mordon, Villeneuve D'Ascq; Jean-Marc Brunetaud, La Madeleine; Hubert Guillet, Saint Michel Sur Orge, all of France

[73] Assignee: Institut National De La Sante Et De La Recherche Medicale, Paris, France

[21] Appl. No.: 971,987

[22] PCT Filed: Apr. 16, 1992

[86] PCT No.: PCT/FR92/00345
§ 371 Date: Feb. 19, 1993
§ 102(e) Date: Feb. 19, 1993

[87] PCT Pub. No.: WO92/18057
PCT Pub. Date: Oct. 29, 1992

[30] Foreign Application Priority Data
Apr. 22, 1991 [FR] France .................. 91 04950

[51] Int. Cl.⁵ .............................. A61N 5/00
[52] U.S. Cl. .......................... 607/89; 606/2; 606/11
[58] Field of Search ..................... 607/88-94; 606/2, 9, 9-13, 16-19

[56] References Cited
U.S. PATENT DOCUMENTS

| | | |
|---|---|---|
| 4,572,189 | 2/1986 | Smith et al. . |
| 4,640,283 | 2/1987 | Sawa et al. .............................. 605/89 |
| 4,692,924 | 9/1987 | Koizumi et al. .................. 607/89 X |
| 4,887,600 | 12/1989 | Watson et al. . |
| 4,930,505 | 6/1990 | Hatje ..................................... 607/89 |

FOREIGN PATENT DOCUMENTS

| | | |
|---|---|---|
| 0065223 | 11/1982 | European Pat. Off. . |
| 0142671 | 5/1985 | European Pat. Off. . |
| 0324948 | 7/1989 | European Pat. Off. . |
| 2829516 | 1/1980 | Fed. Rep. of Germany . |
| 3024169 | 1/1982 | Fed. Rep. of Germany . |

Primary Examiner—Angela D. Sykes
Attorney, Agent, or Firm—Larson and Taylor

[57] ABSTRACT

The invention relates to a device for heat treatment of tissue. The device comprises a laser (20) provided with means enabling it to emit laser radiation in the form of a sufficient number of pulses to deliver a total energy that provides the heat treatment of the tissues, the device being characterized in that it includes means (30, 40) for adjusting the number and the duration of the pulses, said means enabling at least two pulse sequence groups to be emitted: a first pulse sequence group delivering about 70% to 80% of the total energy, and a second pulse sequence group delivering 30% to 20% of the total energy. The invention makes it possible to shorten the total time required for heat treatment of tissues.

14 Claims, 3 Drawing Sheets

DEVICE FOR TREATING TISSUE BY PULSE SEQUENCE GROUP

The present invention relates essentially to a device for heat treating tissue using two groups of pulse sequences.

From the documents U.S. Pat. Nos. 4,784,132, 4,800,876, and 4,848,336 (Fox) a method and a device are known for heat treating tissue using a laser provided with means enabling it to emit a large enough number of pulses of laser radiation to deliver a total amount of energy that results in said heat treatment of tissues. The laser radiation may be conveyed semi-invasively along a lumen of the body by using a catheter or an endoscope containing at least one optical fiber for transmitting the laser radiation from the source to the tissues for heat treatment. The application essentially described in those documents consists in destroying plates of arteriosclerosis. The energy used per pulse is of the order of 150 mJ to 500 mJ (column 5, line 27 of U.S. Pat. No. 4,848,336).

It is also known from an article by McCord et al. in Symposium Lasers in Medicine and Biology of Jun. 22-25, 1977, at pages 9-1 to 9-10, and in particular at page 9-5, to obtain tissue coagulation by heat treatment using laser radiation, in particular with the help of an argon laser, a $CO_2$ laser, or an Nd:YAG laser, using pulses of a duration of 1 second (s), with a rest period of 1.3 s between pulses. McCord shows that the rest period is not long enough for the cooling to avoid the vaporization temperature. Thus, at page 9-8.4, McCord concludes that it is possible to use trains of pulsed irradiation from a neodymium YAG (Nd:YAG) laser while avoiding surface vaporization only when a sufficient amount of rest time is allowed between successive pulses, and this has the major drawback of giving rise to treatment periods that are too long, and that are unacceptable in practice.

An object of the present invention is thus to solve the novel technical problem consisting in providing a solution enabling heat treatment of tissue to be performed by pulsed laser radiation while requiring only a minimum amount of treatment time per point.

The present invention must also solve this novel technical problem by means of a solution that is versatile and that makes it possible either to perform tissue coagulation, or else vaporization, at the option of the practitioner.

The present invention must also solve this novel technical problem by means of a solution enabling the temperature of the tissue to be maintained either in the coagulation range or else in the volatilization range.

Another object of the present invention is to solve the above-specified novel technical problem by providing a solution which enables pulses of variable duration to be used, in particular by enabling them to be grouped together in pulse sequence groups.

Another object of the present invention is to solve the novel technical problem specified above by providing a solution which enables the practitioner to be provided with means that are easy, effective, and reliable for performing heat treatment of tissue with prior programming of a pulse sequence as a function of the looked-for clinical effect, mainly coagulation or volatilization of tissues, and as a function of the nature of the tissues to be treated, for example a tumor of the stomach or of the liver, a colon tumor, or neurosurgery.

All of these technical problems are solved in satisfactory manner for the first time by the present invention which is flexible in use, facilitating the performance of heat treatments of tissue by the practitioner, and in particular using language adapted to the practitioner.

Thus, in a first aspect, the present invention provides a device for heat treating tissue comprising a laser provided with means enabling laser radiation to be emitted in the form of pulses in sufficient number to deliver a total amount of energy that causes said heat treatment to be performed on tissues, the device being characterized in that it includes means for adjusting the number and the duration of the pulses, said means enabling at least two pulse sequence groups to be emitted, a first pulse sequence group delivering about 70% to 80% of the total energy and a second pulse sequence group delivering 30% to 20% of the total energy.

In particular, said total energy advantageously lies between about 20 J and about 200 J.

In an advantageous embodiment, the energy per pulse in the first group lies in the range about 10 J to about 100 J.

In another advantageous embodiment, the energy per pulse in the second group lies in the range about 2 J to about 40 J. Thus, the pulse energy of the second group is less than the pulse energy of the first group.

In another advantageous embodiment, the total energy delivered by the first pulse sequence group is sufficient to heat the treated tissue into the coagulation temperature range, the energy of each pulse in the second group serving to maintain the temperature of the tissues in the coagulation temperature range. Usually, the total energy delivered to reach the coagulation temperature range usually lies between 20 J and 120 J. This tissue coagulation temperature range typically lies between 50° C. and 70° C.

In another advantageous embodiment, the total energy delivered by the first pulse sequence group enables the treated tissue to be heated into the tissue volatilization temperature range and the energy of each pulse in the second group maintains tissue temperature in the volatilization temperature range. Usually, the minimum energy necessary for reaching the volatilization temperature range lies between about 30 J and about 200 J as a function of the nature of the tissues. The volatilization temperature range of tissues typically lies between 100° C. and 120° C.

In an advantageous embodiment of the invention, the device includes automatic control means for performing the various pulse sequences, which means are programmed in advance.

In a preferred embodiment, said automatic control means comprise a memory containing a certain number of sequences that are predefined as a function of the nature of the tissues to be treated and of the desired clinical effects. Thus, the device of the invention preferably contains in its memory at least two treatment programs per type of tissue to be treated, enabling either coagulation or volatilization to be performed on each tissue.

According to a particular characteristic, the first above-mentioned pulse sequence group comprises one or more pulses of duration no greater than 200 ms, and preferably about 100 ms.

In another particular embodiment, the pulse power in the first group is greater than 100 W, and even more preferably lies in the range 100 W and 1000 W, and better still in the range 100 W and 500 W.

In yet another particular embodiment, the duration of each pulse in the second group is less than the duration of any of the pulses in the first group. In particular, the pulse duration of one or more pulses of the second group lies in the range 5 ms to 50 ms Advantageously, the inter-pulse duration in the second pulse group lies in the range two times to twenty times the duration of the preceding pulse.

In another particularly advantageous embodiment of the invention, after the two above-mentioned pulse sequence groups, a rest stage is provided which preferably has a minimum duration of about 300 ms In another advantageous embodiment of the invention, the laser radiation is implemented to perform point heat treatment requiring the two above-mentioned sequence groups to be performed for each point, while the rest stage allows the practitioner to displace the laser radiation from one given treatment point to the following treatment point.

In a preferred embodiment, the laser radiation is transmitted via at least one optical fiber, thereby facilitating displacement of the laser radiation by the practitioner.

In a preferred embodiment of the invention, the total treatment duration for the above-mentioned first and second pulse groups is less than about 1.5 s.

In yet another particularly preferred embodiment of the invention, the total treatment duration per above-mentioned tissue point is compatible with the breathing rhythm of the patient being treated. The rest time typically lies in the range about 200 ms to about 1 s, and preferably in the range 400 ms to 600 ms.

In yet another advantageous embodiment of the invention, the device includes means for issuing an audible or visible warning throughout the time pulses are being emitted in the above-mentioned first and second groups, said means for issuing an audible or visible warning being inactive during the rest stage, thereby constituting means that make it easy for the practitioner to synchronize displacement of the laser radiation from one treatment point to another.

In an embodiment of the invention that is also advantageous, said device includes means for detecting the breathing rhythm of the patient under treatment and for synchronizing the above-mentioned pulse sequence groups as a function of said breathing rhythm so as to deliver the above-mentioned two groups of pulse sequences only during the rest stage of the breathing rhythm.

In yet another advantageous embodiment of the invention, said device includes means enabling the laser radiation to have a power rise time of about 100 W/ms.

In another advantageous embodiment, the laser is a laser that emits continuous type radiation and which is over-excited by temporarily increasing the current flowing through an excitation lamp for the crystal. Advantageously, the laser emits radiation at about 1060 nm or 1320 nm, in particular by using a neodymium YAG (Nd-YAG) crystal or an erbium YAG (Er-YAG) crystal or a Holmium-YAG crystal.

In yet another advantageous embodiment of the invention, the device includes means enabling the temperature of the tissues to be measured after each pulse sequence group and enabling the subsequent pulse sequence group(s) to be modified as a function of the detected temperature observed in this way. Temperature detection means are well known to the person skilled in the art. As preferred temperature detection means, mention may be made of means for detecting tissue temperature without making contact, either by infrared detection, or by reflection measurement, or by colorimetry. This may be performed either by using optical sensors such as optical fibers, or by cameras that detect the heating temperature of the tissues. Other devices include pyrometers.

It will thus be understood that the present invention makes it possible to solve the above-specified novel technical problems and thereby provides the practitioner with means that are easy, quick, versatile, and reliable for performing heat treatment on tissue, and that is done in a manner that is extremely accurate since such treatment can be performed by points of a size that may optionally be adjustable at will, e.g. by using optical fibers of various diameters. A typical value for the dimension of a treated point is about 4 mm.

The present invention will also be easily understood with reference to the accompanying figures that show the presently preferred embodiment of a device for heat treating tissue in accordance with the present invention, which is given purely by way of example and is not limiting on the scope of the invention in any way.

DETAILED DESCRIPTION OF EMBODIMENTS

Figure 1:
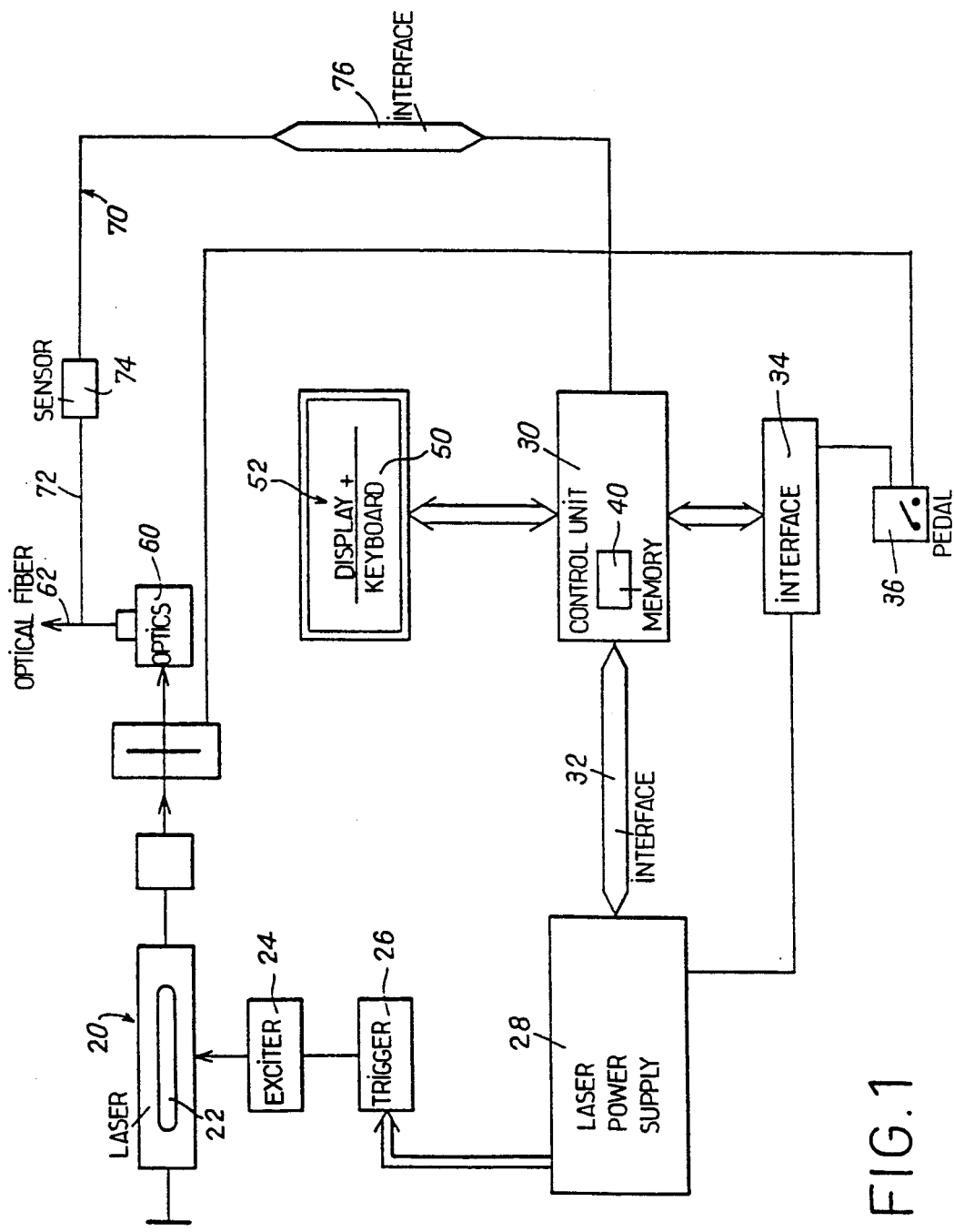
FIG. 1 is a block diagram of a device in accordance with the present invention for heat treatment of tissues.

Overall reference numeral 10 in FIG. 1 designates a device of the present invention for heat treatment of tissues, comprising a laser head 20 containing a suitable crystal 22, well known to the person skilled in the art. For example, the crystal 22 may be of the Nd-YAG or of the Er-YAG or of the holmium-YAG type. The crystal may be excited by an excitation lamp 24 triggered by a trigger device 26 itself powered by a laser power supply device 28 well known to the person skilled in the art and triggered by a control unit 30 that may, for example, include a microprocessor or a microcomputer having appropriate interfaces such as 32 in the form of a bus, for example, and/or 34, in particular for enabling the practitioner to stop and operation, e.g. by a pedal control 36 or by some other equivalent means. The control unit 30 naturally controls all of the operations, including triggering and stopping. Advantageously, the control unit 30 includes at least one memory 40 which may be active or passive in type and which includes one or more programs containing a plurality of predefined pulse sequence groups, as a function of various treatment parameters which include both the nature of the tissue to be treated and also the desired clinical effect, in particular whether the tissue is to be coagulated or volatilized.

For example, these parameters may be input by means of a keyboard 50 communicating with the central control unit 30 and advantageously associated with display means 52, well known to the person skilled in the art.

Naturally, the laser head delivers laser radiation L in a manner well known to the person skilled in the art, e.g. via an appropriate optical system 60 which injects the laser energy (in this case preferably into an optical fiber 62 for transmitting the laser energy to the point of the tissue to be treated), with treatment being performed either outside the body or else in a semi-invasive manner, e.g. by endoscopy. Temperature detection means 70 may also be provided comprising, for example, optical fiber means 72 combined with a sensor 74 and transmitting corresponding data via an interface 76 to the control unit 30. This data can then be processed by the control unit 30 on the basis of programs contained in its memory 40.

It will also be understood that the laser power supply 28 is designed so as to include means making it possible to achieve a laser pulse response time of 100 W/ms to 200 W/ms.

Thus, using the device of the present invention for heat treating tissue, it is possible to perform the following heat treatments, described with reference to accompanying FIGS. 2 to 5:

I - Coagulation treatment of stomach tissue

Figure 2:
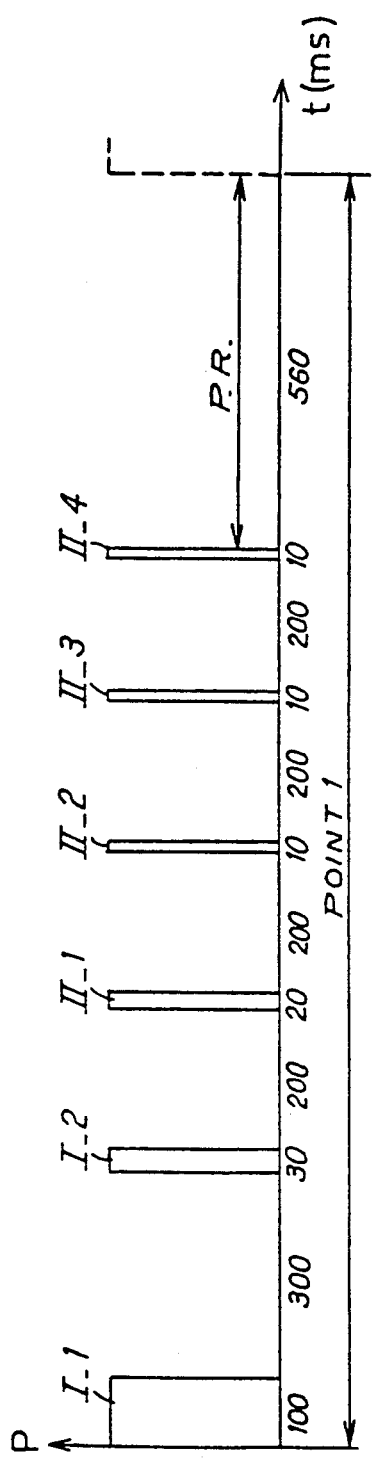
FIG. 2 shows two pulse sequence groups used per treatment point, in this case for performing coagulation treatment of tissues.

To do this, a first pulse sequence as shown in FIG. 2 is provided, comprising, in practice, two pulses given respective references I-1 and I-2 and having different pulse durations, with the first pulse I-1 having a pulse duration of 100 ms, a power of 500 W, and delivering 50 J of energy. This first pulse I-1 is followed by a rest period of 300 ms, and then by a second pulse I-2 having a duration of 30 ms, having the same 500 W power, and delivering an additional 15 J of energy, followed in turn by a rest period of 200 ms, after which a second pulse sequence group is performed given reference II, comprising four individual pulses referenced II-2, II-3, II-4, and II-5, respectively, the first pulse II-2 of the second group having a duration of 20 ms, and the three following pulses being of equal 10 ms duration. These four pulses are separated by rest times of 200 ms. Finally, after the second type II pulse group, there is a rest stage referenced PR of duration 560 ms prior to restarting the operation for another point of tissues to be coagulated.

Figure 3:
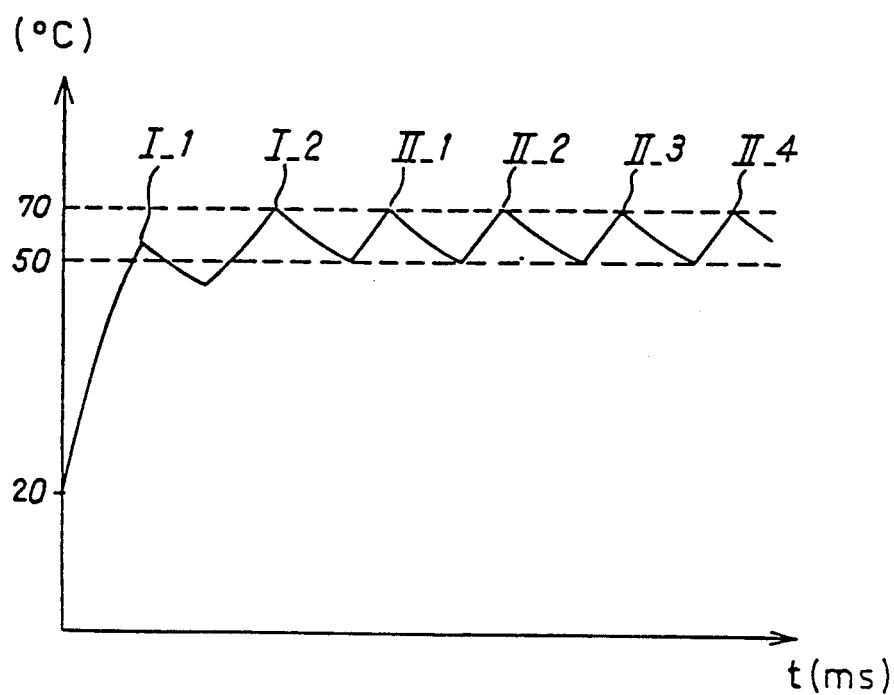
FIG. 3 shows the curve of temperature as a function of time, that results on sending the two pulse sequence groups of FIG. 2, showing that the coagulation temperature range lies between about 50° C. and 70° C.

FIG. 3 is a graph showing how the temperature obtained on the tissues during treatment varies as a function of time expressed in milliseconds, where the temperature peaks achieved on each of the pulses shown in FIG. 2 can be seen.

It can be seen that pulses I-1 and I-2 in the first group enable the tissue coagulation temperature range to be reached, whereas the pulses in the type II second group enable the tissues to be maintained in the coagulation temperature range, which in this case is not less than 50° C., and not more than 70° C.

Figure 4:
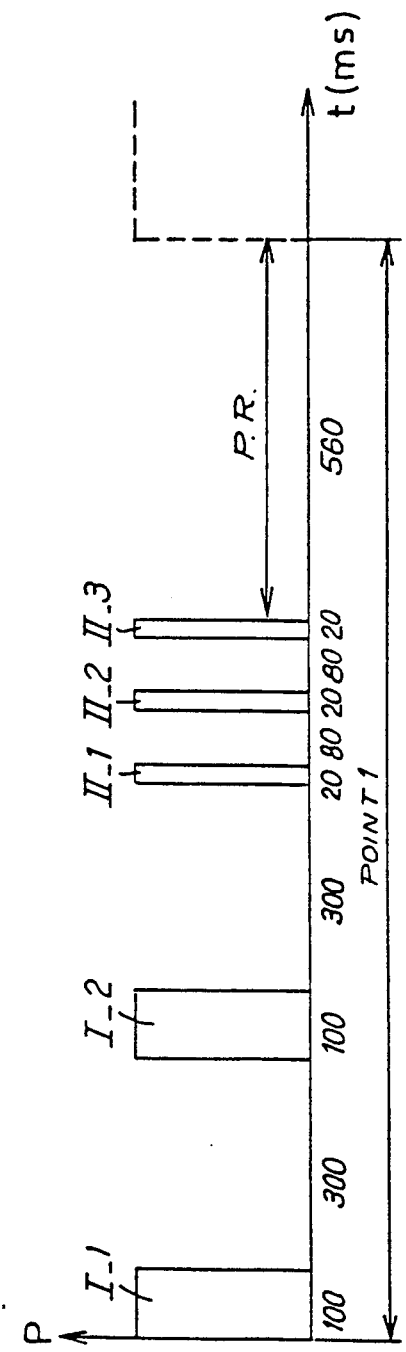
FIG. 4 shows a second group of two pulse sequences predefined for the purpose of achieving tissue volatilization of each treatment point.

Similarly, FIG. 4 shows the cycle for treating stomach tissue to achieve volatilization of the tissues and likewise comprising two groups given overall references I and II, each pulse within a group being given a respective reference 1, 2 or 1, 2, 3.

Figure 5:
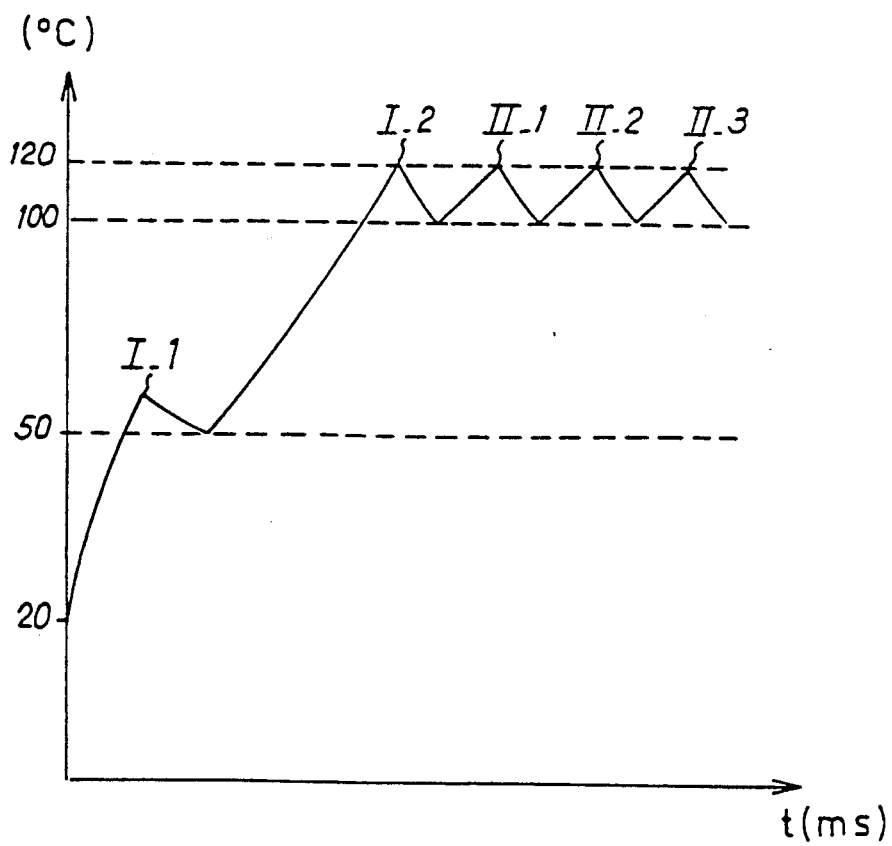
FIG. 5 shows the curve of temperature as a function of time that results from the pulse sequence group shown in FIG. 4, with a tissue volatilization range lying between about 100° C. and about 120° C.

Also, in similar manner to FIG. 3, FIG. 5 is a graph showing how the temperature of the tissues varies as a result of each pulse.

It will be observed that in the same manner, the pulses of the first group enable the tissues to be raised to the volatilization temperature range, which is not less than 100° C., while the pulses in the second group enable the tissues to be maintained at a temperature in the tissue volatilization temperature range, i.e. in the range about 100° C. to about 120° C.

The total cycle time required for treating each tissue point is thus greatly reduced. The total duration of the treatment cycle per point is thus advantageously less than 1.5 s, and even after the rest period PR is added thereto, can remain below 2.2 s, thus enabling the cycle comprising the two pulse groups and the rest time to be performed within a breathing cycle, thereby making it possible to perform rapid treatment on a tumor of relatively large area, which is not possible using prior art devices.

In the same manner, it is possible to perform heat treatment of colon tissues.

We claim:

1. A method for heat treating biological tissue, comprising the steps of:
   (a) illuminating a localized region of the tissue with a sequence of laser pulses in sufficient number to deliver a total amount of energy that causes said heat treatment to be performed at said localized region, said sequence comprising:
   a first group of laser pulses delivering 70% to 80% of the total energy of the pulse sequence, each pulse in said first group having a duration not greater than 200 ms and each delivering an amount of energy in the range from 10 J to 100 J, and
   a second group delivering 20% to 30% of the total energy of the sequence, consisting of pulses each having an energy in the range from 2 J to 40 J, the duration of any one of the pulses in the second group being lesser than the duration of any one of the pulses in the first group; and
   (b) repeating step (a) for illuminating another localized region of the biological tissue to be treated.

2. Method according to claim 1, wherein the duration of each said pulse in the first group is between 5 and 15 ms.

3. Method according to claim 1, wherein the time period between successive said pulses of the second group is between two times and twenty times the duration of each said pulse in the second group and wherein each sequence is followed with a rest period at least equal to 300 ms.

4. Method according to claim 2, wherein each said sequence has a total duration lower than 1.5 s.

5. Method according to claim 1 for treatment of biological tissue by volatilization, wherein the amount of energy delivered by the first group of pulses in each said sequence is sufficient for heating the treated region of the tissue into a volatilization temperature range of the tissue and the amount of energy of each said pulse in the second group is sufficient for maintaining the tissue temperature in the volatilization temperature range while lower than the value which would be necessary for heating the tissue to the volatilization temperature range from the natural biological temperature of the tissue.

6. Method according to claim 5, wherein the total energy delivered by the first group of laser pulses is of 130 to 200 J.

7. Method according to claim 1, for heating the tissue into the coagulation temperature range, wherein the accumulated energy delivered by the pulses of the first group is of from 20 to 120 J and the amount of energy delivered by each said pulse in the second group is sufficient for maintaining the treated region in the coagulation temperature range but insufficient for heating the treated tissue from the normal biological temperature to the coagulation temperature range.

8. A method according to claim 1, wherein the total energy delivered by the first group of laser pulses is selected to heat the treated tissue into the coagulation temperature range and the energy of each pulse in the second group is selected to maintain the tissue temperature in the coagulation temperature range.

9. A method according to claim 1, wherein the total energy delivery by the first group of laser pulses is selected to heat the treated tissue into the volatilization temperature range and the energy of each pulse in the second group is selected to maintain the tissue temperature in the volatilization temperature range.

10. A device for heat treating biological tissue, comprising:

a laser provided with means for causing it to generate a beam of light energy;

a control means coupled to said laser for controlling delivery of light energy by said laser in the form of successive sequences of pulses;

manually operated means for initiating and stopping operation of said device; and memory means in said control unit, for storing a plurality of predetermined instructions each identifying a pulse duration, a pulse energy and a spacing between pulses of a respective group of laser pulses;

means for selection of groups within said memory, said control means causing said laser to deliver successive sequences each consisting of a first one of said groups and second one of said groups, wherein the pulses in the first group deliver 70% to 80% of the total energy of the pulse sequence, each pulse in said first group having a duration not greater than 200 ms and delivering an amount of energy in the range from 10 J to 100 J, and the pulses in the second group deliver 20% to 30% of the total energy of the sequence and consist of pulses each having an energy in the range from 2 J to 40 J, the duration of any one of the pulses in the second group being lesser than the duration of any one of the pulses in the first group.

11. A device according to claim 10, further comprising optical means for transmitting laser radiation from said laser to a treatment point.

12. A device according to claim 10, wherein said laser is a continuous laser and is over-excited by a temporary increase in current flowing through a crystal excitation lamp constituting said means for causing the laser to deliver said beam.

13. A device according to claim 10, further comprising means for emitting an audible or visible warning signal throughout the entire time during which the pulses in the above-mentioned first and second groups are being emitted, and for emitting no audible or visible warning signal during the rest stage.

14. A device according to claim 10, further comprising automatic control means for controlling the performance of the various pulse sequences which are programmed in advance.

* * * * *